United States Patent
Alfadul et al.

(10) Patent No.: US 8,980,099 B2
(45) Date of Patent: Mar. 17, 2015

(54) MAGNETIC EXTRACTANTS, METHOD OF MAKING AND USING THE SAME

(71) Applicant: King Abdulaziz City for Science and Technology, Riyadh (SA)

(72) Inventors: Sulaiman M. Alfadul, Riyadh (SA); Abdulrahman I. Alabdula'aly, Riyadh (SA); Mujahid A. Khan, Riyadh (SA)

(73) Assignee: King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 13/925,240

(22) Filed: Jun. 24, 2013

(65) Prior Publication Data

US 2013/0277314 A1    Oct. 24, 2013

Related U.S. Application Data

(62) Division of application No. 12/967,778, filed on Dec. 14, 2010.

(51) Int. Cl.
| | |
|---|---|
| *C02F 1/48* | (2006.01) |
| *B03C 1/01* | (2006.01) |
| *B03C 1/28* | (2006.01) |
| *B03C 1/30* | (2006.01) |
| *B82Y 30/00* | (2011.01) |
| *C07F 15/02* | (2006.01) |

(Continued)

(52) U.S. Cl.
CPC ... *C02F 1/48* (2013.01); *B03C 1/01* (2013.01); *B03C 1/288* (2013.01); *B03C 1/30* (2013.01); *B03C 2201/18* (2013.01); *B03C 2201/26* (2013.01); *B82Y 30/00* (2013.01); *C02F 1/288* (2013.01); *C02F 1/488* (2013.01); *C02F 1/681* (2013.01); *C02F 2305/08* (2013.01); *C07F 15/025* (2013.01); *Y10S 977/773* (2013.01); *Y10S 977/811* (2013.01); *Y10S 977/838* (2013.01); *Y10S 977/896* (2013.01)
USPC ........... 210/671; 977/773; 977/811; 977/838; 977/896

(58) Field of Classification Search
CPC ........... B03C 1/01; C02F 1/288; C02F 1/488; C02F 1/681; C02F 2305/08
See application file for complete search history.

(56) References Cited

U.S. PATENT DOCUMENTS

| | | | |
|---|---|---|---|
| 2,398,725 A | * | 4/1946 | Schutte .......................... 208/26 |
| 4,294,705 A | * | 10/1981 | Hellestam .................... 210/695 |
| 4,554,088 A | | 11/1985 | Whitehead et al. |

(Continued)

OTHER PUBLICATIONS

Alfadul, Sulaiman Mohammed. Using Magnetic Extractants for Removal of Pollutants From Water Via Magnetic Filtration. Dissertation, Oklahoma State University. Ann Arbor: ProQuest/UMI, 2006. (Dissertation No. 3246857).*

(Continued)

*Primary Examiner* — Matthew O Savage
(74) *Attorney, Agent, or Firm* — Andrew M. Calderon; Roberts Mlotkowski Safran & Cole, P.C.

(57) ABSTRACT

A water treatment composition capable of effectively adsorbing pollutants from water is described. The composition includes magnetic extractants, which comprise magnetite nanoparticles containing functional groups. The composition is used to remove from water and aqueous streams oils and other contaminants. A process for removing contaminants from water and apparatus used in the process are also described.

14 Claims, 11 Drawing Sheets

(51) Int. Cl.
*C02F 1/28* (2006.01)
*C02F 1/68* (2006.01)

(56) References Cited

U.S. PATENT DOCUMENTS

| | | | |
|---|---|---|---|
| 4,695,392 | A | 9/1987 | Whitehead et al. |
| 5,244,580 | A | 9/1993 | Li |
| 5,397,476 | A | 3/1995 | Bradbury et al. |
| 5,441,648 | A * | 8/1995 | Lidzey .......... 210/695 |
| 5,855,790 | A | 1/1999 | Bradbury et al. |
| 6,099,738 | A | 8/2000 | Wechsler et al. |
| 6,103,127 | A | 8/2000 | Pourfarzaneh |
| 6,261,471 | B1 | 7/2001 | Tsuda et al. |
| 6,296,937 | B2 | 10/2001 | Pryor et al. |
| 6,596,182 | B1 * | 7/2003 | Prenger et al. ......... 210/798 |
| 7,153,435 | B2 | 12/2006 | Prenger et al. |
| 7,169,618 | B2 | 1/2007 | Skold |
| 7,520,994 | B2 | 4/2009 | Dong et al. |
| 7,686,960 | B2 | 3/2010 | Cort |
| 2008/0035577 | A1 | 2/2008 | Brook-Levinson et al. |
| 2008/0073280 | A1 | 3/2008 | Cort |
| 2009/0321363 | A1 | 12/2009 | Murai et al. |
| 2010/0012880 | A1 | 1/2010 | Rampersaud et al. |
| 2010/0051557 | A1 | 3/2010 | Etemad et al. |
| 2010/0059448 | A1 | 3/2010 | Fujieda et al. |
| 2010/0072141 | A1 | 3/2010 | Lopes |
| 2010/0096312 | A1 | 4/2010 | Lopes |

OTHER PUBLICATIONS

Liu, Jing-fu, Zong-shan Zhao, and Gui-bin Jiang. "Coating Fe3O4 magnetic nanoparticles with humic acid for high efficient removal of heavy metals in water." Environmental science & technology 42.18 (2008): 6949-6954.*

"Origin and Chemistry of Humic Acids", http://www.pharmawerk-weinboehla.de/english/humine/humin2.html, 1972.*

Final Office Action for related U.S. Appl. No. 12/967,778 dated Nov. 8, 2013.

Non-final Office Action for related U.S. Appl. No. 12/967,778 dated Jul. 8, 2013.

Alfadul S. M., "Using Magnetic Extractants for Removal of . . . Via Magnetic Filtration", Dissertation, Oklahoma State University, Ann Arbor:ProQuest/UMI, 2006, p. 1-118.

Y. Shi et al., "$CoFe_2O_4$ nanoparticles prepared by the mechanochemical method", Journal of alloys and compounds 308.1 (2000): 290-295.

Office Action for related U.S. Appl. No. 13/925,291 dated Jan. 3, 2014, 11 pages.

Office Action for related U.S. Appl. No. 13/925,350 dated Jan. 6, 2014, 12 pages.

Office Action for related U.S. Appl. No. 12/967,778 dated Mar. 27, 2014, 6 pages.

Final Office Action for related U.S. Appl. No. 13/925,350 dated Apr. 25, 2014, 20 pages.

Final Office Action for related U.S. Appl. No. 13/925,291 dated Apr. 29, 2014, 19 pages.

Notice of Allowance for related U.S. Appl. No. 13/925,350 dated Nov. 24, 2014, 10 pages.

Notice of Allowance for related U.S. Appl. No. 13/925,291 dated Nov. 21, 2014, 7 pages.

Office Action for related U.S. Appl. No. 13/925,291 dated Aug. 26, 2014, 5 pages.

Office Action for related U.S. Appl. No. 13/925,350 dated Aug. 28, 2014, 5 pages.

Notice of Allowance for related U.S. Appl. No. 12/967,778 dated Aug. 21, 2014, 9 pages.

* cited by examiner

MAGNETIC EXTRACTANTS, METHOD OF MAKING AND USING THE SAME

FIELD OF THE INVENTION

The invention relates to magnetic extractants which can be used to purify water and aqueous streams and to a treatment process, which uses the extractants to remove contaminants from water or the aqueous streams (also referred to herein as aqueous fluids). These magnetic extractants are capable of selectively adsorbing oils discharged into oceans, seas, or rivers and/or pollutants contained in industrial or domestic wastewater, surface runoffs and ground waters or other aqueous fluids. Accordingly, the treatment method employing these extractants can remove the pollutants, including oils from the wastewater and aqueous streams.

BACKGROUND

Aqueous fluids, including wastewater produced by industrial enterprises, such as factories, as well restaurants, households and from many other sources, are likely to contain pollutants, such as oils, e.g., mineral and vegetable oils, and crude oil, are often discharged into oceans, seas or rivers which may cause serious ecological problems. When the seas or rivers are polluted with large amounts of oils, the oils are generally enclosed by oil fences to prevent them from dispersing, and then are recovered. Further, the oils are often adsorbed, solidified and recovered by use of oil-gelling agents. However, if the rivers run fast or the oceans and seas are turbulent, e.g., because of high tides or extreme weather conditions, such as hurricanes, it is difficult to adsorb and solidify the oils. Accordingly, under such conditions, it may be difficult to contain and solidify the oils. As a result, oil slicks are formed which are washed up on the beaches and adversely affect seabirds and/or marine life.

On the other hand, in a water purification system for treating wastewater (such as industrial and domestic wastewaters) containing a small amount of oils dispersed therein, the wastewater is generally filtered through a filter to remove the oils. However, since the filter in the system has a tendency to clog with the oils, it is necessary to change the filter frequently. Hence, considerable cost and effort are required to maintain the system. Further, if the wastewater contains a large amount of oils, the oils and the water may separate to form upper and lower layers, respectively. If the wastewater containing such layers is filtered, the filter often clogs. To avoid the clogging it is necessary to perform time and effort consuming pretreatments of such wastewater. The pretreatments may include spreading, inorganic or organic adsorbents, such as silica and pearlite, or organic water purification agents comprising oleophilic polymers, on the wastewater before the filtration. However, it is difficult to collect and recover the organic adsorbents and polymers, and the inorganic adsorbents are generally poor in oil adsorbability.

JP-A 2000-176306 discusses a method of recovering oil floating on water surface. Heavy oil is recovered by dispersing a magnetic body and magnetically separated by a recovery apparatus mounted on a recovery ship. The magnetic body is provided with heightened affinity for the heavy oil by coating surface of a fine magnetite particle with a hydrophobic coating of stearic acid. The magnetic attractive force of the recovery apparatus to the magnetite affects the heavy oil through the stearic acid, and sea water and the heavy oil are efficiently separated by magnetic force.

Fujieda et al., U.S. Patent Application Publication 2010/0059448 discusses a water treatment composition and method of using it to treat water containing pollutants. The composition comprises magnetic particles, which include magnetic powder subjected to surface treatment with a particular organometallic compound. The composition can be rapidly separated by a magnetic force. The organometallic compound comprises a metal atom connected to an alkoxy group and an amphipathic organic group. The magnetic substance may be a material exhibiting ferromagnetism at room temperature, such as any ferromagnetic material, e.g., iron, iron alloy, magnetite and others. The sizes and shapes of the magnetic particles can be controlled, and the mean size is preferably 0.2 micrometer to 5 millimeters. The magnetic powder may comprise magnetic granules having surfaces subjected to hydrophobic treatment with alkoxysilane compounds, e.g., methyltrimethoxysilane, methyltriethoxysilane, phenyltrimethoxysilane and phenyltriethoxysilane. The water treatment composition, is used in a water treatment method to remove pollutants, such as organic pollutants or particularly oils, e.g., mineral oils, animal and vegetable fats and oils, hydrocarbons and aromatic oils.

Murai et al., US Patent Application Publication US 2009/0321363 discusses particles and a method for treating water with the particles similar to that of Fujieda. After the surfaces of the magnetic particles are treated with silane coupling agents containing amino groups, the amino groups are reacted with halogenated hydrocarbons having hydrocarbon chains (i.e., hydrophobic moieties). Normally, the mean size of the magnetic particles is 0.1 to 1000 μm.

Bradbury, et al., U.S. Pat. No. 5,397,476, discusses a method for removing pollutant ions from an aqueous solution, which comprises contacting the solution with particles of a composite magnetic resin which includes magnetic particles embedded in an organic polymeric matrix. The organic polymeric matrix either contains or has attached to it sites which are selective for the pollutant ions in the presence of other ions, which are not desired to be removed. In the next step, composite magnetic resin particles are separated by magnetic filtration from the solution. Then, the separated composite magnetic resin particles are subjected to regeneration using an appropriate regenerant solution, and are separated from the regenerant solution and recycled.

Etemad et al., US Patent Application Publication 2010-0051557 discusses a process for eliminating heavy metal cations from an aqueous medium. The process comprises two stages: in the first stage, iron oxide nanoparticles, such as magnetite, are suspended in an aqueous medium contaminated with the heavy metal cations, and in the second stage the solution is brought into contact with a ferromagnetic matrix (or a paramagnetic matrix) magnetized by an outside magnetic field. The heavy metal cations are deposited on the matrix under the imposed magnetic field and then separated from the matrix. The heavy metal cations are cadmium, lead and copper.

Prenger et al., U.S. Pat. No. 6,596,182 discusses a process for removing heavy metals from water which includes the steps of introducing magnetite to a quantity of water containing heavy metal and mixing the magnetite with water, so at least a portion of the heavy metal is bound to the magnetite. The magnetite and the absorbed metal are removed from the water by application of a magnetic field, e.g. by flowing the water through a solid magnetized matrix, such as a steel wool, so that the magnetite magnetically binds to the solid matrix. Alternatively, the magnetized matrix is subject to an externally applied magnetic field. Once the magnetite and the heavy metal is bound to the matrix, it can be removed and disposed of. The magnetite may be formed in situ.

Rampersaud et al., US Patent Application Publication US 2010/0012880, discusses particles which may have a magnetic particle having a protective layer and a hydrophilic and a hydrophobic portion.

However, a need still exists in the art to overcome deficiencies and limitations of previously-existing methods.

SUMMARY

The invention in one embodiment is directed to a method of producing magnetic extractants, which includes dissolving in an aqueous medium a salt of Fe (II) chloride and a salt of Fe (III) chloride about 2:3 mole ratio, while mixing, to form an aqueous solution of $FeCl_2$ and $FeCl_3$. Subsequently, a base is added to the aqueous solution at conditions sufficient to cause precipitation of magnetite nanoparticles. The precipitated magnetite nanoparticles are washed to remove excess amount of any undesired ions. Then, the magnetite nanoparticles are dried and ground. The ground and dried magnetite nanoparticles, have extensive hydroxyl groups. These magnetite nanoparticles are then functionalized by subsequently treating the magnetite nanoparticles with a silane reagent containing functional groups or a polymer to produce magnetic extractants.

In another embodiment, the invention is directed to the magnetic extractants produced by the above method.

In yet another aspect, the invention is directed to a process for removing impurities from an aqueous fluid containing impurities, comprising dispersing the magnetic extractants in an aqueous fluid containing impurities, thereby adsorbing the impurities on surfaces of the magnetic extractants. The magnetic extractants with the adsorbed impurities are collected and recovered by magnetic force.

In a further embodiment, the invention comprises an apparatus for making magnetic reactants, which includes a vessel equipped with a stirring means and a reflux, a dosing unit, a mixer unit, operatively connected to the dosing unit, and a separation unit operatively connected to the mixer unit. The apparatus further includes a means for applying magnetic field to the separation unit, e.g., a magnet or an electromagnet, and a collection unit operatively connected to the separation unit. The collection unit collects used magnetic reactants. A clean water tank is included in the apparatus for collecting a substantially clean aqueous fluid, which is substantially free of impurities.

Yet another embodiment is directed to an apparatus for making magnetic reactants, which includes a hybridization oven that comprises one or more hybridization tubes. The apparatus further includes a dosing unit and a mixer unit operatively connected to the dosing unit. A separation unit is operatively connected to the mixer unit. Also included in the apparatus of this embodiment is a means for applying magnetic field to the separation unit, e.g., a magnet or an electromagnet. Further included is a collection unit operatively connected to the separation unit, which collects used magnetic reactants, and a clean water tank for collecting from the collection unit a substantially clean aqueous fluid, which is substantially free of impurities.

BRIEF DESCRIPTION OF SEVERAL VIEWS OF THE DRAWINGS

The present invention is described in the detailed description which follows, in reference to the noted plurality of drawings by way of non-limiting examples of exemplary embodiments of the present invention.

In FIG. 2, "MNP" means magnetite nanoparticle. The graph of FIG. 2 shows relationship between intensity of the radiation (Y-axis) and detector angle 2-theta (X-axis).

In FIG. 4, R and R' are functional groups.

In FIGS. 6 and 7, M means magnetization, emu/g means electromagnetic units per gram, and H(Oe) means magnetic field strength. In FIG. 7 H=90 Oe means that magnetic field strength (H) is fixed during the test at 90 Oersted (Oe). FIG. 7, shows the extent of magnetization of $Fe_3O_4$ nanoparticles in a field of 90 Oe measured on a super conducting quantum interference device magnetometer. The absence of a well defined maximum in the ZFC curve (of FIG. 7) indicates that $Fe_3O_4$ nanoparticles exhibit blocking temperature above room temperature. It is known that the maximum of the ZFC curve for a collection of super paramagnetic, non interaction single-domain nanoparticles is dependent on the size of nanocrystals and their degree of clustering, as well as on the mutual dipolar interaction between them.

DETAILED DESCRIPTION

Figure 1:
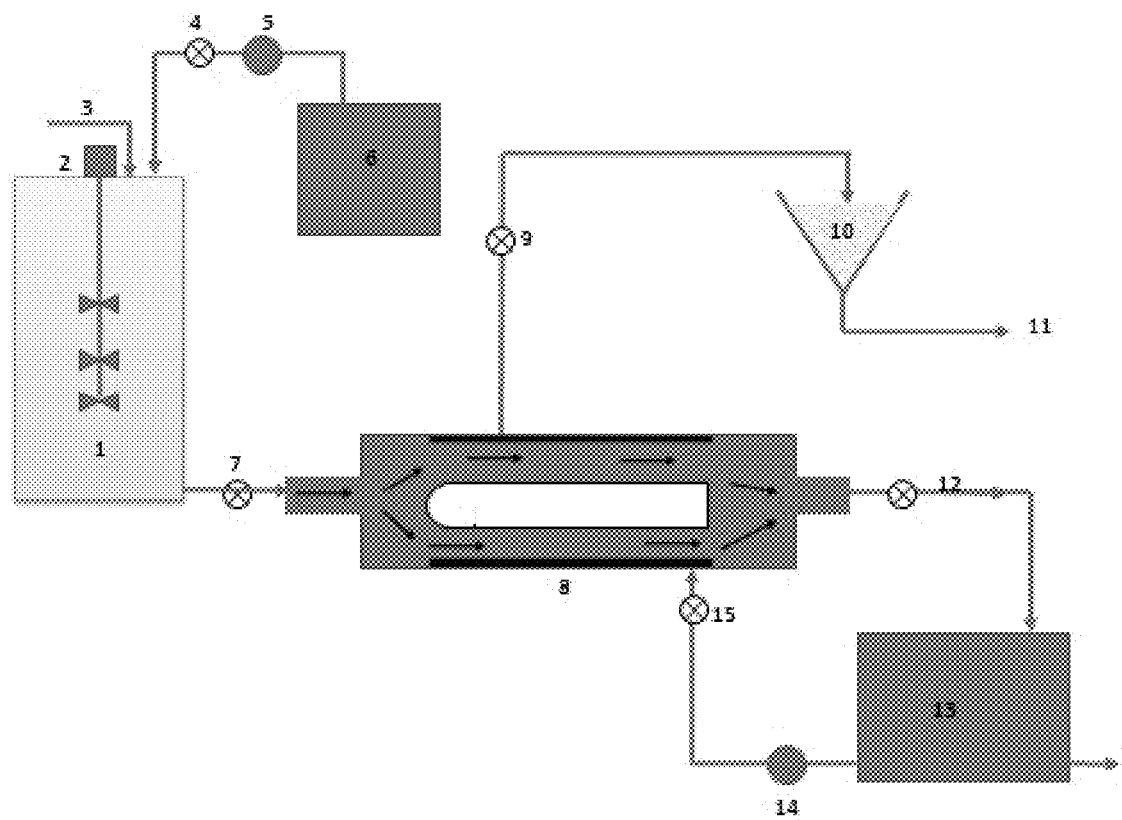
FIG. 1 shows a schematic view of a system in which water or aqueous fluids can be treated with the magnetite nanoparticles according to one embodiment of the invention.
Figure 2:
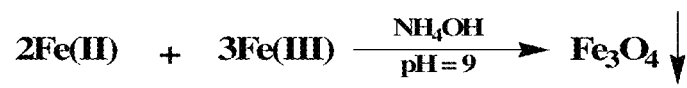
FIG. 2 describes chemical reaction of the Fe(II) and Fe(III) salts to produce magnetite nanoparticles ($Fe_3O_4$) according to this invention. The crystallite size of the resulting magnetite nanoparticles, in one exemplary embodiment measured by the Warren-Averbach method, was 10 nm.
Figure 2:
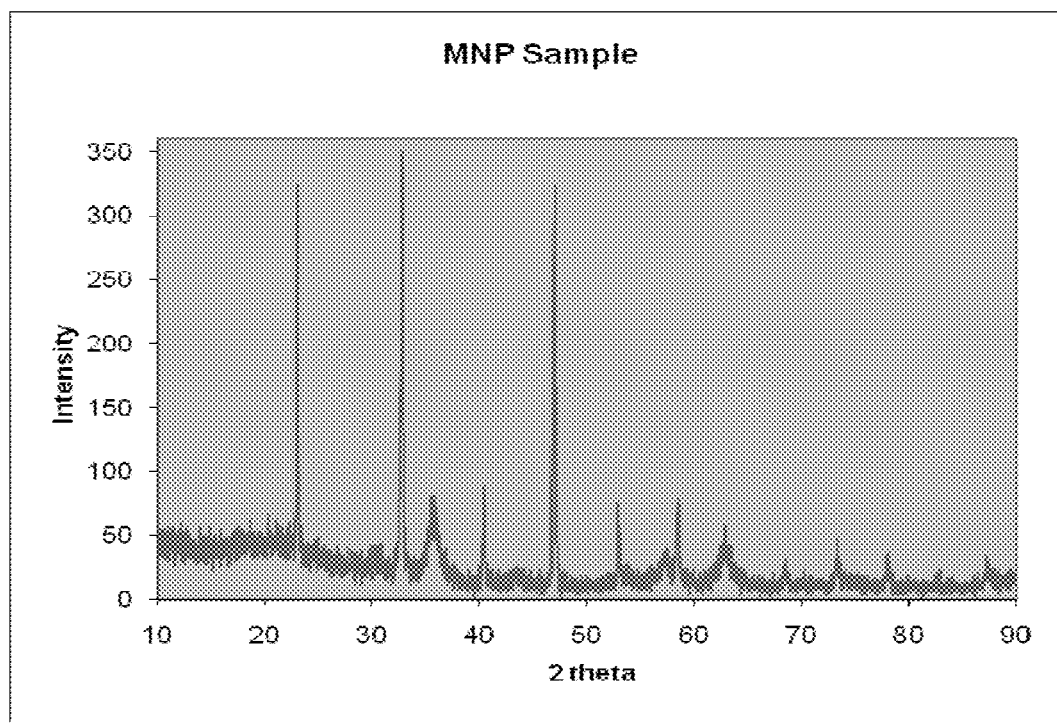
Figure 3:
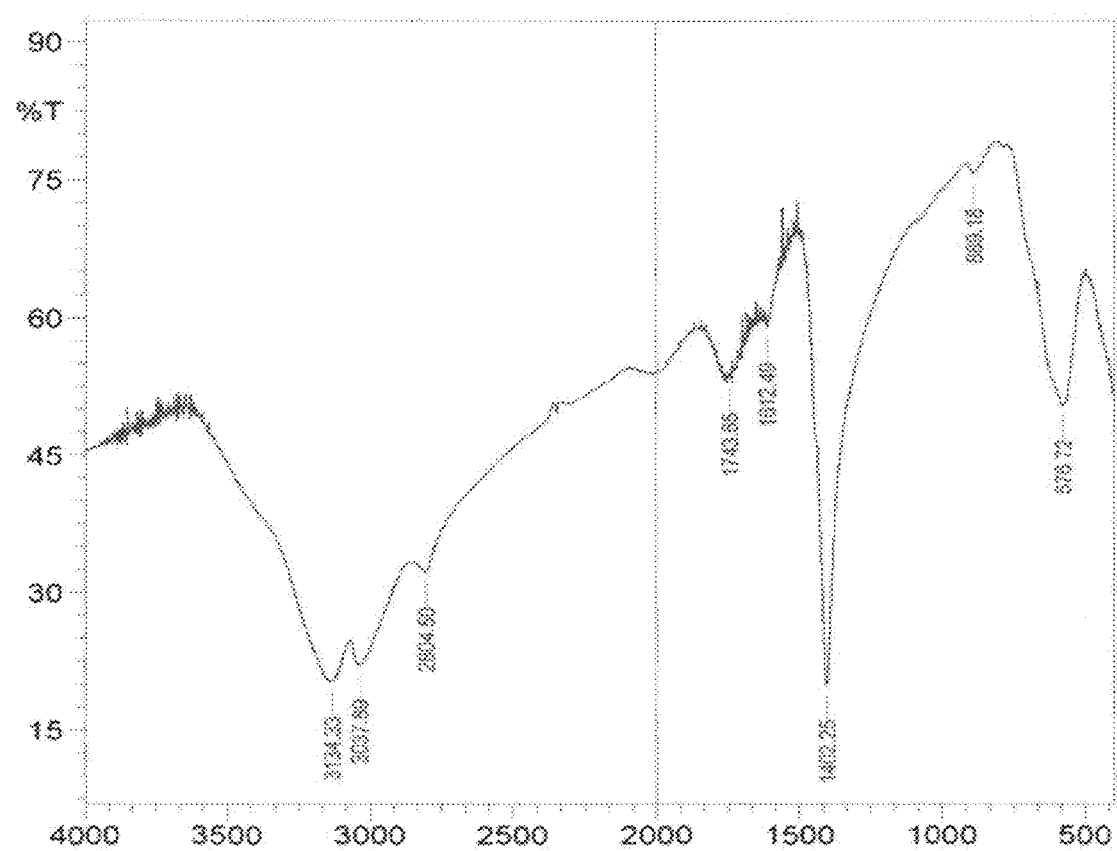
FIG. 3 shows spectra of Fourier transform infrared (FTIR) spectroscopy analysis of the magnetite nanoparticles of the invention, which indicate extensive hydroxyl groups on the surface of the particles.
Figure 4:
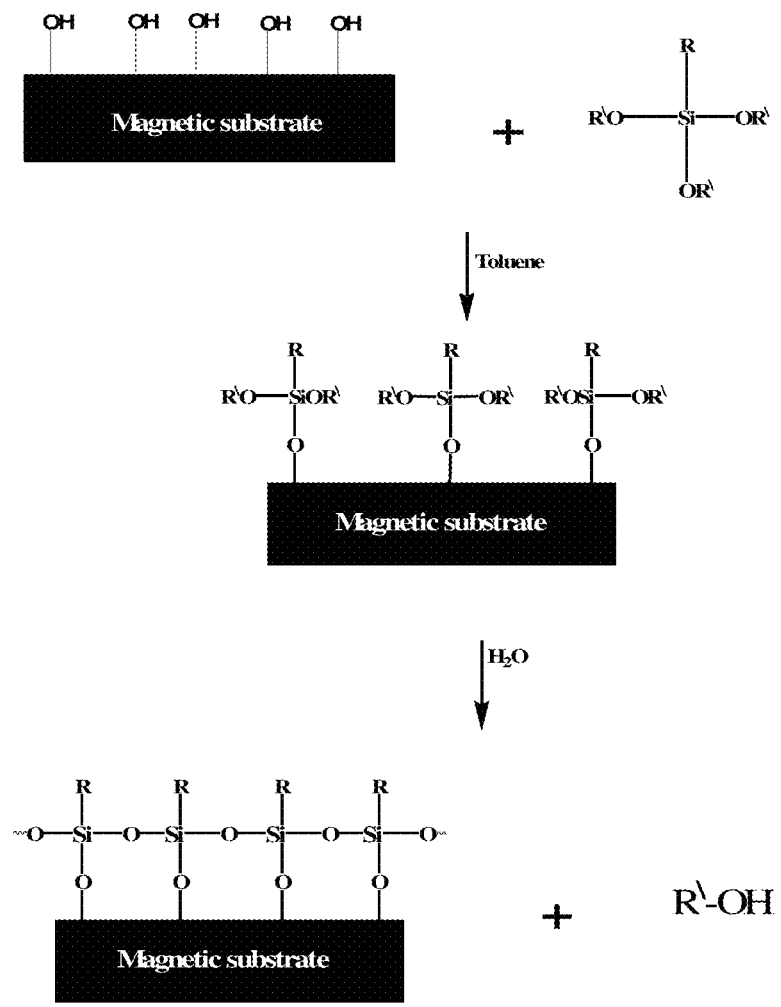
FIG. 4 shows schematically chemical reactions of magnetite nanoparticles (magnetic substrate) to functionalize the nanoparticles and obtain magnetic extractants, at relatively low temperature (i.e., between about 60° C. and about 80° C.). The amount of water which may be adsorbed by the magnetic extractants depends on the ability of the reactants to adsorb water from the surrounding atmosphere during preparation since the synthesis was not performed under an inert gas and in situ water was produced during the preparation.
Figure 5:
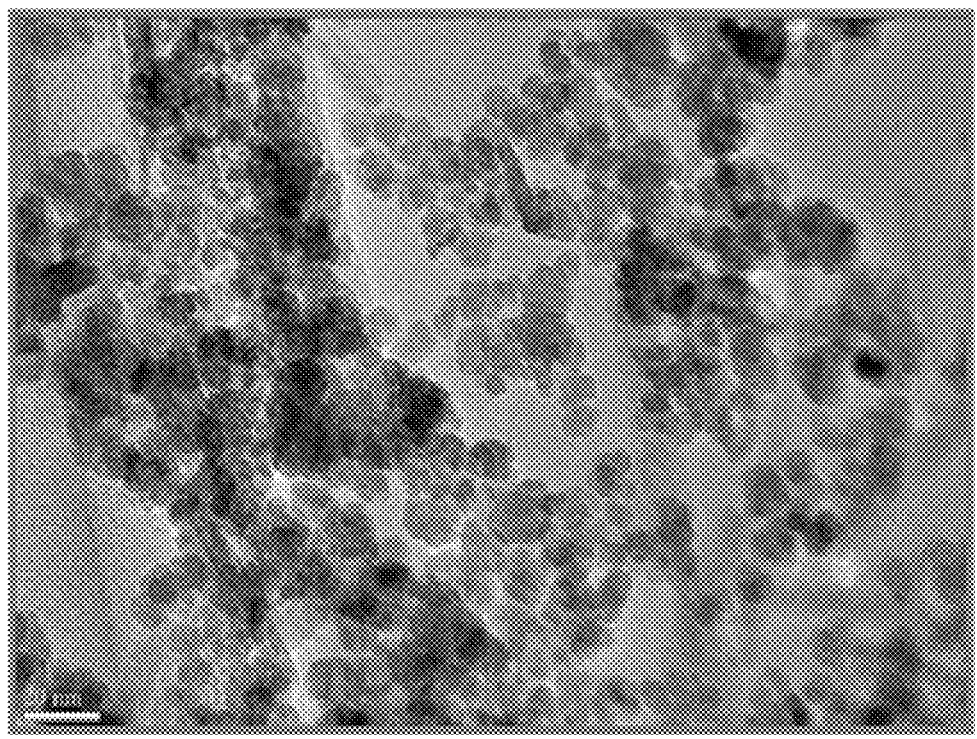
FIG. 5 are images of transmission electron microscopy (TEM) of the MN-amine indicating a particle size range from 5-15 nm, and showing extent of aggregation for MN-amine particles.

In the specification, including Figures, "MN" means "magnetite nanoparticle" When, "MN" is combined with a functional group, e.g."MN-amine" it designates magnetic extractants which include the functional group, e.g., amine.

Magnetic Extractants for Water Purification and Method for Making Thereof

The magnetic extractants for water and aqueous streams purification comprise magnetite nanoparticles which are subjected to surface treatment with a particular functional group which is likely to bind with the particular impurity in water or the aqueous fluid being treated, i.e., the magnetic extractants are likely to adsorb the particular impurity. The magnetite nanoparticles, prior to their functionalization, have a significantly high number of hydroxyl groups on their surface. Such nanoparticles also have high specific surface area (SSA) (i.e., about 47 $m^2/g$) and high magnetic strength. The magnetic extractants have specific surface area of about 15 to about 26 $m^2/g$ and high magnetic strength.

The magnetic extractants nanoparticles have mean particle size of less than about 25 nanometers (nm), such as about 5 to about 24 nm, about 5 to about 15 nm, or about 10 nm, and are likely to have superparamagnetism properties (i.e., that magnetic behavior exhibited by iron oxides with crystal size less than about 300 A°, which is characterized by responsiveness to a magnetic field without resultant permanent magnetization). An advantage associated with the superparamagnetic properties is that the nanoparticles can be repeatedly exposed to magnetic fields without becoming permanently magnetized, which prevents them from magnetically aggregating. Hence, the nanoparticles can be re-dispersed and reused. Even after functionalization (e.g., with a silane reagent), the magnetic extractants nanoparticles of the invention exhibit a high surface area per unit of weight, and correspondingly high coupling capacity to contaminants. The magnetic extractants comprise magnetite nanoparticles coated with a layer of different chemicals to treat different contaminants, e.g., organic species, inorganic species and/or radioactive species.

The aqueous fluids that may be purified, i.e., treated, in the process and system of this invention are substantially all types of aqueous fluids and industrial wastewater, such as without limitation, sewage water, nuclear wastewater, oil spills, all types of industrial wastewaters, domestic wastewaters, surface runoffs, and ground waters.

As discussed above, the magnetic extractants comprise two components: a) the magnetite nanoparticles, and b) functional groups deposited on surface of the magnetite nanoparticles. The magnetite nanoparticles may be synthesized.

The synthesized magnetite nanoparticles are prepared by adding to an aqueous medium (usually at ambient temperature) and with agitation Fe (II) and Fe(III) salts (e.g., $FeCl_2$ and $FeCl_3$) in such amounts that the resulting aqueous solution includes about 2.5 to about 4% of the Fe (II) salt (e.g., $FeCl_2$) and about 1 to about 3% of the Fe(III) salt (e.g., $FeCl_3$). Under agitation, a base, e.g., concentrated $NH_4OH$ (such as 14% aqueous solution of $NH_4OH$), is added to the solution at ambient temperature to increase the pH to about 8-10, such as pH of 9, which causes the precipitation of magnetite nanoparticles. The aqueous medium may be water.

The ratio of Fe(II) to Fe(III) in the aqueous medium may be adjusted by adjusting proportions of the iron chlorides to obtain a desired ratio of iron oxides in the product magnetite nanocrystals. In general, the Fe(II) to Fe(III) molar ratio in the aqueous solution is about 2:3. The precipitated slurry is then settled, decanted, and washed with a 5% ammonium hydroxide solution to remove an excess of undesired ions, e.g., ammonium and chloride ions. The settling, decanting and washing steps may be repeated to reduce the level of undesired ions. If needed, centrifugation may be used instead of the settling and decantation steps to accelerate the method. The precipitate, containing the magnetite nanoparticles, is then dried in a suitable manner. Subsequently, the dried magnetite nanoparticles are ground to produce magnetite nanoparticles having the mean particle size discussed herein. The grounded magnetite nanoparticles are used without any additional treatment, other than deposition of functional groups and any additional treatments discussed herein. Thus, in contrast to known methods, the grounded particles of this invention are not functionalized in the same step as they are produced.

The magnetite nanoparticles are ground or comminuted in any suitable manner, e.g., using a mortar, a ball mill or a hammer mill. The mean particle size can be measured in any suitable manner, e.g., TEM, Scanning Electron Microscopy (SEM) or Dynamic Light Scattering (DLS).

The dried magnetite nanoparticles can be functionalized by any suitable method. The magnetite nanoparticles have extensive hydroxyl groups on the surface due to their method of synthesis described herein and thus can be easily coupled with silane reagents by the formation of Fe—O—Si covalent bonds. The treatment with a silane reagent containing functional groups or a polymer can be carried out by several embodiments.

In one embodiment, the dried magnetite nanoparticles are functionalized by treating the magnetite nanoparticles, which have extensive hydroxyl groups on their surface, with a silane reagent (e.g., a toluene or xylene solution of a silane reagent) containing functional groups to produce the magnetic extractants of this invention.

In one embodiment, the dried magnetite nanoparticles, which have the negative charge, due to the extensive presence of hydroxyl groups are placed in one or more hybridization tubes. Then a toluene or xylene solution of a silane reagent or a polymer is introduced into the hybridization tubes. The toluene or xylene solution of a silane reagent contains about 2% of the silane reagent. The silane reagent may be any suitable silane reagent, e.g., octadecyltrimethoxysilane, to produce a magnetite particle with octadecyl functional group (MN-octadecyl); 3-glycidoxypropyl-trimethoxysilane to produce a magnetite particle with an epoxide functional group (MN-epoxide); and/or 3-aminopropyl trimethoxy silane to produce a magnetite particle with an amine functional group (MN-amine). Any suitable hybridization tubes may be used. In one aspect of the invention, 100 ml hybridization tubes are used.

After the treatment with the toluene (or xylene) solution of the silane reagent or polymer is completed, the hybridization tubes are transferred to a hybridization oven. The tubes, together with their contents, are rotated in the hybridization oven (e.g., at 60 strokes/min for 24 hours) until substantially all or all of the hydroxyl groups residues are bound with the functional groups. The resulting magnetite nanoparticles with the functional groups are isolated by filtration, washed extensively with toluene to remove unattached molecules of the functional groups and dried at 60° C. The hybridization tubes seal and protect the reaction from humidity. This produces magnetite nanoparticles (of the magnetic extractants) having a thin film coating of silsesquioxane of the general formal $RSiO_{1.5})_X$ where R is hydrogen or an alkyl, alkene, aryl, or arylene group, and x is the number of repeat units.

The hybridization oven mixes uniformly and homogeneously all the reactants in the hybridization tubes. In one embodiment, the operating conditions of the hybridization oven are: temperature maintained at 60° C., the hybridization tubes are rotated at 60 strokes/min, and the treatment is carried out for 24 hours. All the used hybridization tubes may be of the same size and type. The number and type of hybridization tubes may be selected based on operational parameters, such as type and volume of reactants.

In an alternative embodiment, the treatment with a silane reagent or a polymer is carried out in a vessel equipped with a mechanical stirring means, such as a stirrer, and a reflux. In this embodiment, the dried magnetite nanoparticles, which have the negative charge, are placed in the vessel and a toluene or xylene solution of a silane containing functional groups or a polymer is added to the vessel. The magnetite nanoparticles and the toluene or xylene solution containing functional groups or a polymer are introduced into the vessel with rigorous mixing provided by the mechanical stirrer and the reflux. The rigorous mixing is maintained until substantially all or all of the hydroxyl groups residues are bound with the functional groups, to produce magnetite nanoparticles containing the functional groups. These magnetite nanoparticles are isolated by filtration, washed extensively with toluene to remove loose (unattached) molecules of the functional groups and dried, e.g., at 60° C.

If a polymer is used to functionalize the magnetite nanoparticles, suitable polymers are those that have appropriate functional groups for this invention.

The invention is also directed to the magnetic extractants produced by the method(s) described herein.

The functionalized magnetite nanoparticles are referred to herein as magnetic extractants. The functional groups that are coated onto the nanoparticles are such that they will bind to:
1. organic species;
2. inorganic species;
3. radioactive species; and
4. any other species in the contaminated water.

Exemplary functional groups include aldehydes, amides, carboxylic functional groups, ketone, and amine groups. The magnetite nanoparticle surface can be functionalized with various groups by treatment with a reactive functional group which is suitable to bind a particular contaminant. For example, amines (mono, di- and tri-amines) can be used for removal of heavy metals, radioactive species and organics. Also large aliphatic groups can be used for removal of organic species. A mixture of functional groups may be deposited onto the magnetite nanoparticles.

The thus-prepared magnetic extractants for water purification may contain small amounts of the functionalizing agent, i.e., the silane reagent or polymer, and the magnetite nanoparticles in uncombined forms. It is possible to reduce the content of the uncombined forms of such agents and magnetite nanoparticles, e.g., by controlling the conditions of functionalization reaction or by any other suitable means.

Instead of magnetite nanoparticles, other magnetic materials may be used, which are preferably materials exhibiting ferromagnetism at room temperature, but they by no means restrict embodiments of the present invention. Accordingly, any ferromagnetic material can be employed. Examples of the ferromagnetic material other than magnetite include iron, iron alloy, ilmenite, pyrrhotite, magnesia ferrite, cobalt ferrite, nickel ferrite, and barium ferrite. Among them, ferrites having excellent stability in water are preferred because objects of the present invention can be effectively achieved. For example, magnetite ($Fe_3O_4$) is not only inexpensive but also stable in water, and further does not contain harmful elements. Hence, advantageously it can be used for water treatment. The magnetic materials useful in this invention may have the shape of powdery granules in various shapes, such as spheres, polyhedrons and irregular forms. The sizes and shapes of the magnetic materials can be properly selected in consideration of production cost and other conditions.

The magnetic extractants may include substances other than magnetic materials. For example, the magnetic extractants may comprise a magnetic material combined with a binder, such as a resin. Regarding magnetic properties of the magnetic extractants, it is only required that they have sufficient magnetic properties so they can be collected and recovered by the use of magnetic force in the water treatment of this invention.

Water Treatment Method

An exemplary water treatment method according to the present invention is used for separating pollutants from water or aqueous fluids containing them. The "pollutants" means substances that are contained in the water or aqueous fluids to be treated that must be removed to enable the water or the fluids to be reused. The water treatment composition (i.e., magnetic extractants) according to the present invention is employed for treating water containing organic pollutants, particularly, oils, which can be adsorbed by the magnetic extractants. Subsequently, the pollutants are removed from the magnetic extractants, so that the extractants can be reused. In this exemplary embodiment "oils" means oils and fats that are generally liquid at room temperature, that are only slightly soluble in water, that have relatively high viscosities and that have specific gravities lower than water. They are, for example, mineral oils, animal and vegetable fats and oils, hydrocarbons, and aromatic oils. Those oils are characterized by chemical groups contained therein, and hence the functional groups deposited on the magnetic extractants are selected so that they would bind to the chemical groups. This exemplary water treatment method may also be used to remove from water other pollutants, e.g., pesticides.

In the water treatment method according to this invention, first the magnetic extractants are dispersed in water containing the pollutants, e.g., oil pollutants. Since the surfaces of the magnetic extractants contain functional groups with affinity to the pollutants, the pollutants are adsorbed on the extractants. The magnetic extractants have oleophilic groups on their surfaces, and hence they adsorb the pollutants. Accordingly, the adsorption ratio of the magnetic extractants is very high, although it depends upon the concentration of the pollutants and upon the amount and surface area of the magnetic extractants particles. If the magnetic extractants are used in a sufficient amount, the pollutants are adsorbed in an amount of generally 80% or more, such as 97% or more, 98% or more, or 99% or more of the pollutants are adsorbed by the magnetic extractants.

After the pollutants are adsorbed, the magnetic extractants are collected and recovered to remove the pollutants from the water. In this step, magnetic force is used to collect the magnetic extractants. Since the magnetic extractants are attracted by magnetic force, they can be easily collected and recovered.

The water treatment method can be used with substantially any reasonable concentration of pollutants in the water. However, if the concentration of pollutants is unusually high, it may be desirable to dilute the pollutants' concentration e.g., by adding clean water to the water or aqueous stream being treated. Of course, the amount of magnetic extractants used may need to be adjusted, based on the concentration of the pollutants.

An exemplary embodiment of the invention is directed to a system and a method (collectively "system") for treating contaminated water, which uses magnetic properties of the magnetic extractants of this invention, coated with different functional groups. The system comprises four main units described with reference to FIG. 1 as follows:

A. a mixer unit 1 (also referred to herein as "a chemical mixing tank with raw water");

B. a separation unit 8 (also referred to herein as "a magnetic filter");

C. a dosing unit 6 (also referred to herein as "extractants tank" which contains the magnetic extractants); and D. a collection unit 10 (also referred to herein as "used extractant collector").

Contaminated water is treated in the mixer unit 1 with magnetic extractants, which had been previously coated with different functional groups, as described above. Thus, the magnetic extractants are comprised of magnetite nanoparticles coated with a layer of functional groups. Initially, the content and nature of contaminants in the water to be treated is determined. Then, an amount of magnetic extractants having functional groups which needs to bind with the contaminants in the water is introduced into the mixer unit from the dosing unit 6. After a suitable residence time in the mixer unit 1, sufficient to bind the extractant particles to the contaminants in the water, a mixture of the contaminated water and the extractants (having the contaminants bound thereto) is conducted to the separation unit 8.

In the separation unit, a magnetic field (produced, e.g., by a magnet or an electric magnet, not illustrated) is activated, which causes the magnetic extractants (with contaminants bound to the extractants) to be retained by the magnetic forces in the separation unit, usually retained against the walls of the separation unit. Purified, clean water passes from the separation unit 8 to a clean water tank 13. When the magnetic field is deactivated, the magnetic extractants (having the contaminants attached thereto) are separated from the walls of the separation unit and flushed to a collection unit 10, by any suitable mechanism, e.g., by mechanical means. A cleaning pump 14 directs a portion of the clean water into the separation unit 8 to flush the used magnetic extractants.

The system also includes an electric mixer 2 and an inlet of raw water (i.e., contaminated water) 3. A dosing pump 5 is used to control the amount and kind of magnetic extractants from the extractants tank 6 to be introduced into the mixer unit 1. A conduit from the extractants tank 6 to the mixer unit 1 includes a valve 4 (e.g., an electric valve). Similarly, electric valves 7, 9, 14 and 15 are installed in conduits between various units as shown in FIG. 1.

To enhance effectiveness of the magnetic force, a magnet in the form of a net or a grid can be installed around any desired portion of, or around the entire separation unit 8. The magnet may be an electromagnet, or a conventional magnet.

The contaminants, e.g. oils, can be recovered, e.g., by washing or extraction of the magnetic extractants in the collection unit 10 with suitable solvents. For example, if contaminants are one or more oils, extraction or washing solvents can be used to recover the contaminants, such as n-hexane and alcohols. This enables the magnetic extractants to be reclaimed, and re-used. After the contaminants are removed, the solvents are sent via a conduit 11 to a waste water receptacle, e.g., a drum (not shown).

The solvents should be selected so that they do not dissolve or remove functional groups from the magnetic extractants. Examples of the solvents include methanol, ethanol, n-propanol, iso-propanol, acetone, tetrahydrofuran, n-hexane, cyclohexane, and mixtures thereof.

EXAMPLES

Example 1

Figure 6:
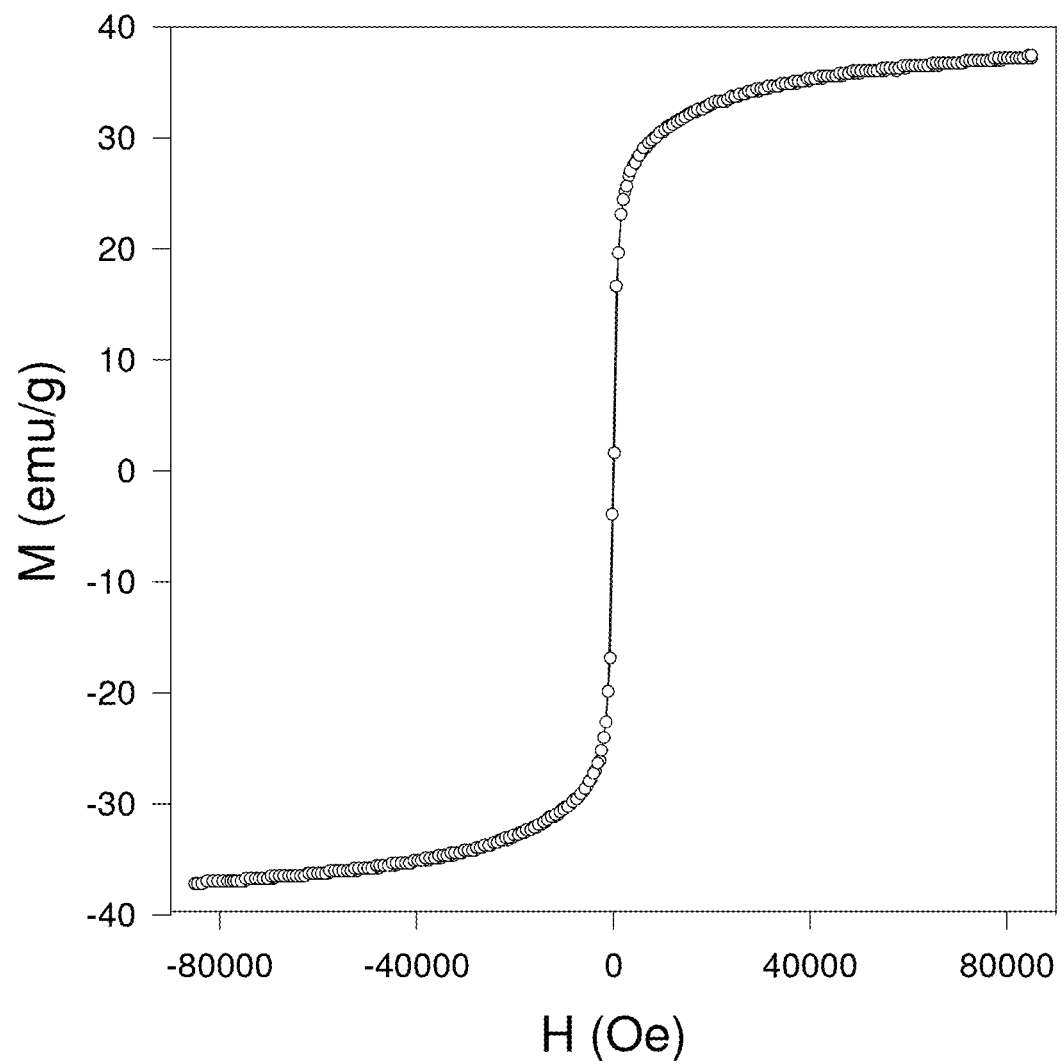
FIGS. 6 and 7 illustrate results of magnetic properties analysis of the magnetite nanoparticles. The magnetic properties of the magnetite nanoparticles of the invention were measured, which show that the nanoparticles have high magnetic forces and superparamagnetism properties, i.e., the nanoparticles respond to a magnetic field without resultant permanent magnetization.
Figure 7:
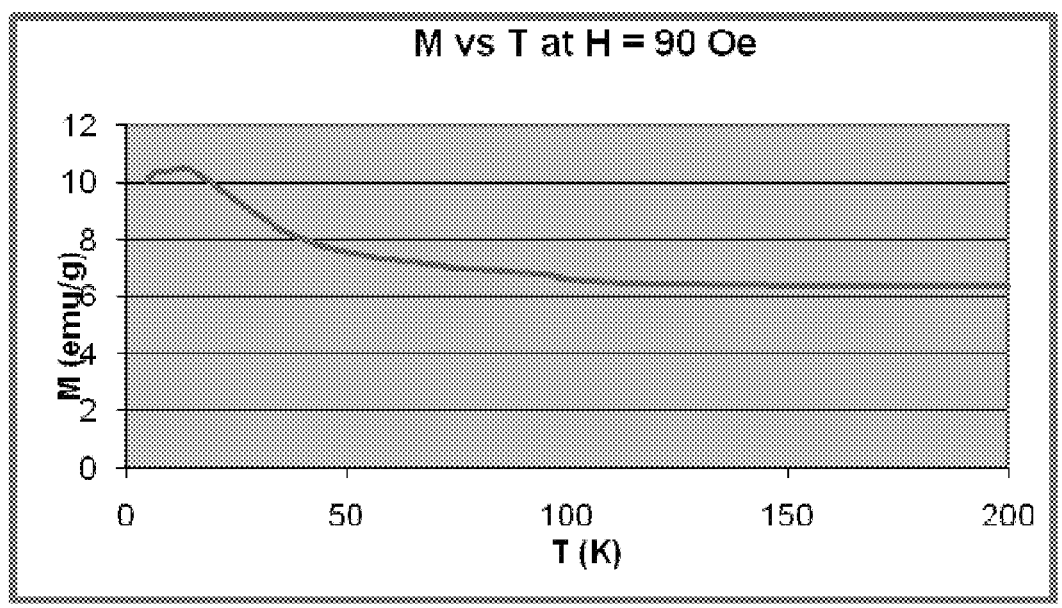

Magnetite nanoparticles were synthesized by adding, with agitation at 60 rpm 3.97 grams of $FeCl_2$ and 8.11 grams of $FeCl_3$ to water in a container. Agitation continued until complete dissolution at room temperature. The resulting aqueous solution contained 6.62% of the Fe (II) salt and 13.52% of the Fe(III) salt i.e., 2:3 mole ratio. Under agitation, concentrated $NH_4OH$ (14% aqueous solution of $NH_4OH$) was added to the solution at ambient temperature to increase pH to 9. After 5 minutes, precipitation of magnetite nanoparticles took place, which had mean particle size 10-70 nm. The precipitated slurry was then settled, decanted, and washed with a 5% ammonium hydroxide solution to remove excess of undesired ions, e.g., ammonium and chloride ions. The precipitate, containing the magnetite nanoparticles, was then dried and the dried magnetite nanoparticles were ground in a mortar to produce magnetite nanoparticles having specific surface area of 47 $m^2/g$. The ground nanoparticles were used, without any additional treatment, other than deposition of functional groups as described in Example 2. Results are shown in FIGS. 6 and 7.

Example 2

10 grams of the dried and ground magnetite nanoparticles of Example 1 were functionalized by treating the nanoparticles, which contained an extensive content of hydroxyl groups on surfaces of the particles, with a toluene solution of a silane reagent containing functional groups to produce the magnetic extractants. The treatment with the silane reagent containing functional groups was carried out as described below.

The dried and ground magnetite nanoparticles, which had the negative charge, were placed in 100 ml hybridization tubes. Then 18 g of a toluene solution containing 5.5% by volume of octadecyltrimethoxysilane was added to each of the hybridization tubes, with stirring, and the stirring continued overnight.

The hybridization tubes were transferred to a hybridization oven. The tubes were rotated in the hybridization oven at 60 strokes/min for 24 hours at 60° C. until substantially all or all of the hydroxyl groups residues of the magnetite nanoparticles were bound with the silane functional groups. The resulting magnetite nanoparticles containing octadecyl functional groups (MN-octadecyl) were isolated by filtration, washed extensively with toluene to remove unattached molecules of the functional groups and dried at 60° C. to produce magnetic extractants. The hybridization tubes sealed and protected the reaction from humidity, which produced magnetic extractants having a thin film coating of silsesquioxane of the general formal $RSiO_{1.5})_X$.

Figure 11:
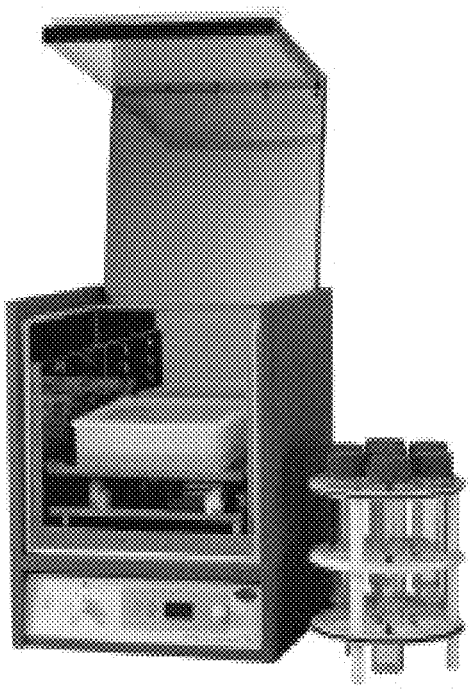
FIG. 11 shows an exemplary hybridization oven which can be used in this invention.

The hybridization oven used in this study was manufactured by Stuart Company. It had a capacity of 2 liter, a temperature range of 8 to 80 C.°, and a rotation speed of 2 to 10 rpm. The oven had a stainless steel interior whereas the door was constructed from a double glazed panel of smoked acrylic and polycarbonate to provide radiation protection, if any. The number and type of hybridization tubes may be selected based on the volume of reactants and other operational parameters. A hybridization oven used in this Example is illustrated in FIG. 11.

The hybridization oven mixed uniformly and homogeneously all the reactants in the hybridization tubes.

In a similar manner, magnetic extractants were prepared with 3-glycidoxypropyltrimethoxysilane to produce a magnetic extractant with an epoxide functional group (MN-epoxide); and with 3-aminopropyl trimethoxy silane to produce a magnetic extractant with an amine functional group (MN-amine).

Specific surface areas of the magnetite of Example 1 and of the three magnetic extractants are shown in Table 1.

Example 3

The magnetic extractants of Example 2 were used in the system and process of this invention to remove contaminants from water.

The system (apparatus) used in this example is illustrated in FIG. 1. 10 g of water contaminated with 31.28 ppm of benzene was introduced into the mixer unit 1. 0.1 g of the MN-octadecyl magnetic extractant of Example 2 was also added to the mixer unit. The contents of the mixer unit were continuously agitated with the electric mixer. After 120 minutes of residence time in the mixer unit, a mixture of the contaminated water and the magnetic extractants (having the contaminants bound thereto) was conducted to the separation unit (or magnetic filter) 8.

In the separation unit, magnetic field, produced by a magnet was activated to produce magnetic field, which caused the MN-octadecyl magnetic extractants (with benzene bound to the extractants) to be retained against walls of the separation unit 8 by the magnetic forces produced by the magnet. The magnet was activated for 20 seconds. Purified, clean water passed from the separation unit to a clean water tank 13. When the electric field was deactivated, the magnetic extractants (having the contaminants attached thereto) were set free from the walls of the separation unit and were removed from the separation unit to a collection unit 10, by shutting valve 12 and opening valves 9 and 15 so a portion of clean water flushed the used extractants.

The benzene contaminant was recovered by washing the magnetic extractants in the collection unit 10 with proper solvents. The magnetic extractants, substantially free of benzene, were reclaimed, and re-used.

Figure 8:
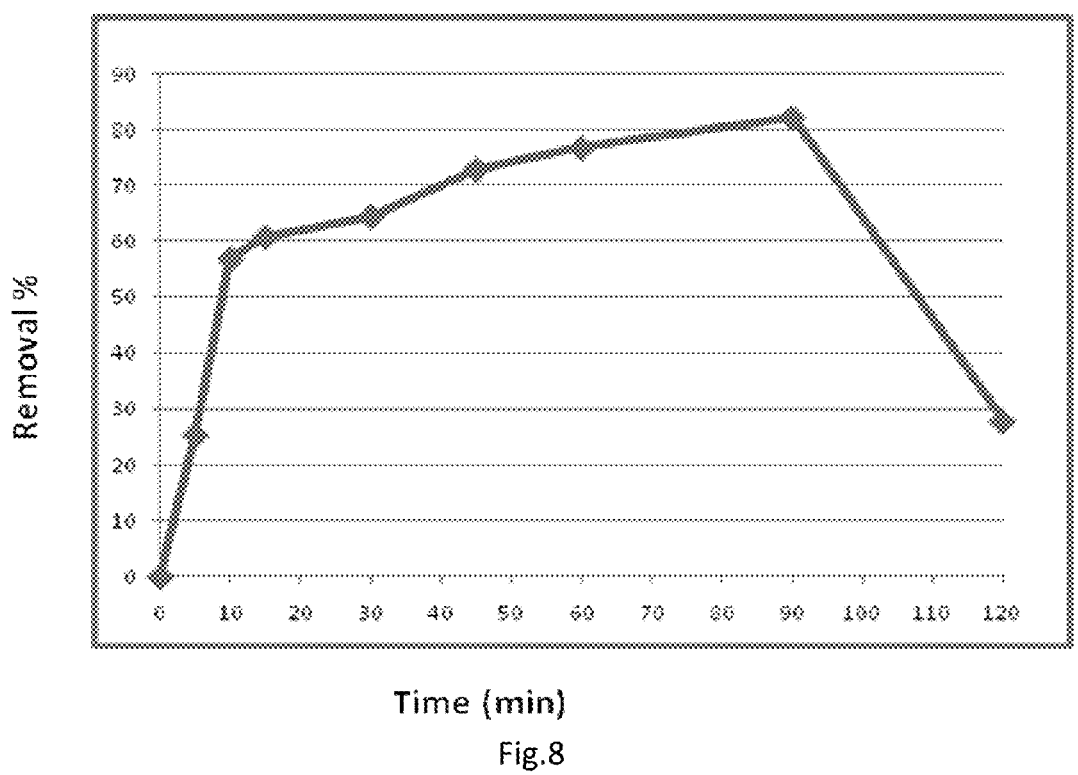
FIG. 8 shows results of removal of benzene (31.28 ppm) from a contaminated aqueous stream using MN-octadecyl.
Figure 9:
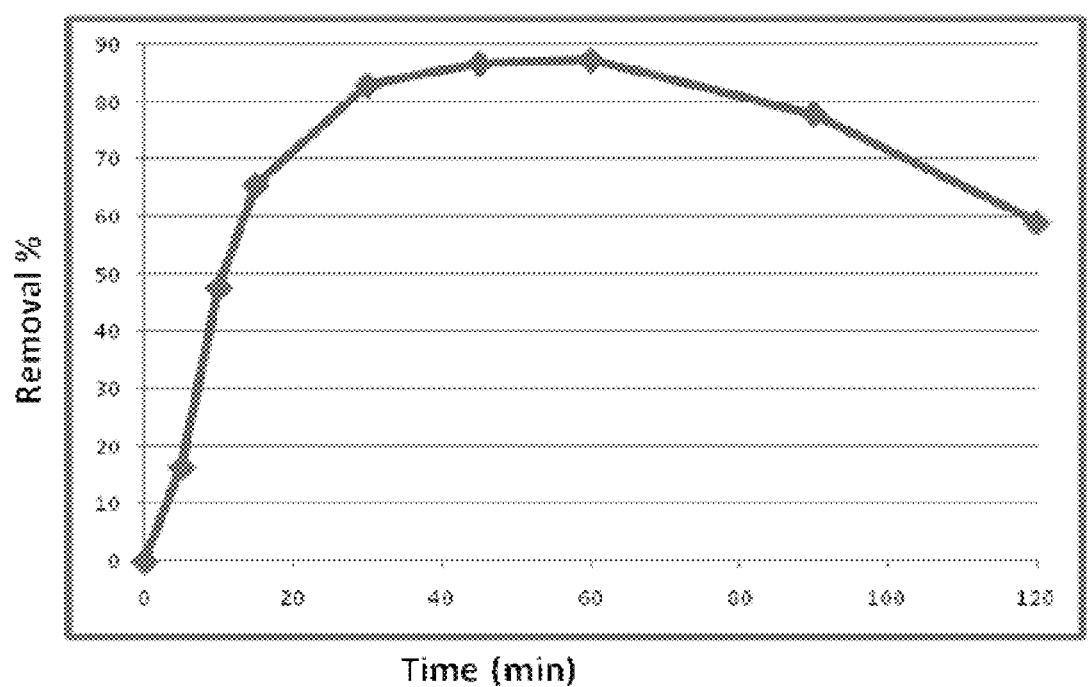
FIG. 9 shows results of removal of benzene (31.28 ppm) using MN-epoxide.
Figure 10:
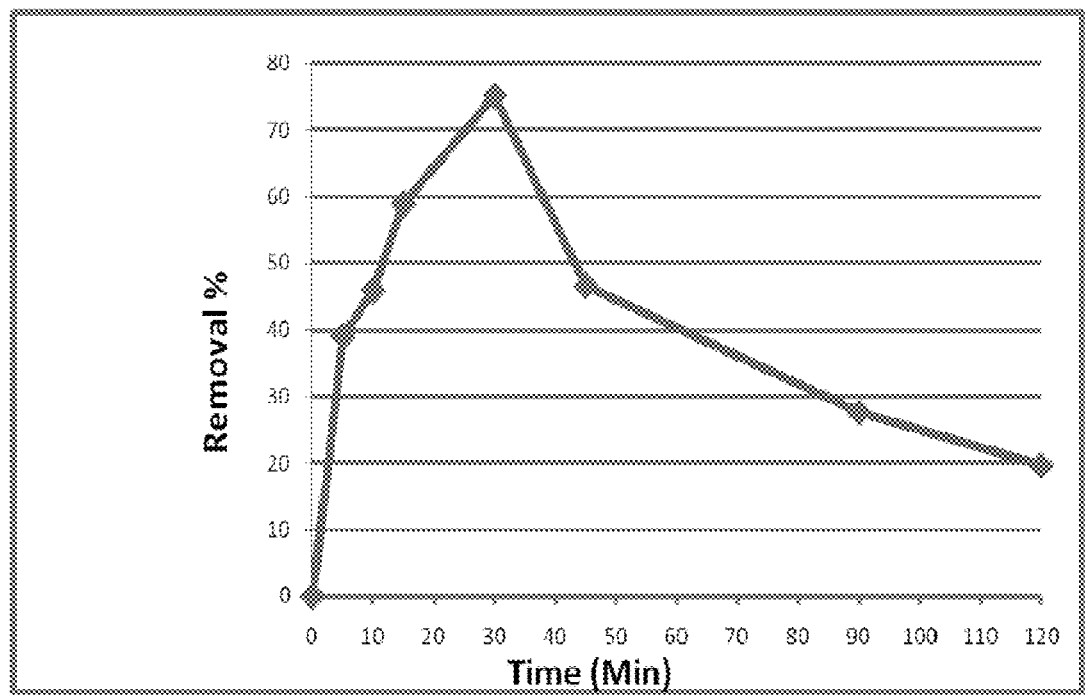
FIG. 10 shows results of removal of benzene (31.28 ppm) using MN-amine.

Two separate samples, each 10 ml, of the same water stream were treated with the MN-epoxide and MN-amine magnetic extractants in a similar manner as described above. The results are summarized in Table 2, and FIGS. 8, 9 and 10.

Example 4

The same magnetic extractants were used in substantially the same process as in Example 3 to remove a variety of pesticides and organic compounds from water streams. Results are summarized in Tables 3 and 4, respectively.

TABLE 1

SPECIFIC SURFACE AREA OF EXTRACTANTS

| Extractant/Magnetite | SSA ($M^2/g$) |
|---|---|
| Magnetite | 46.82 |
| MN-octadecyl | 24.27 |
| MN-epoxide | 21.15 |
| MN-amine | 15.94 |

TABLE 2

REMOVAL OF BENZENE (31.28 ppm) USING SYNTHESIZED EXTRACTANTS

| Weight of the extractant (g) | % Removal MN-octadecyl | % Removal MN-epoxide | % Removal MN-amine |
|---|---|---|---|
| 0.1 | 18.54 | 21.35 | 28.06 |
| 0.2 | 22.12 | 29.22 | 33.98 |
| 0.5 | 29.25 | 30.43 | 37.24 |

TABLE 3

REMOVAL OF SOME PESTICIDES USING SYTHESIZED EXTRACTANTS

| Pesticide | Conc. (ppm) | % Removal MN-octadecyl | % Removal MN-epoxide | % Removal MN-amine |
|---|---|---|---|---|
| Alfa Landane | 0.87 | 36.78 | 41.38 | 45.98 |
| Beta HBC | 5.39 | 35.99 | 7.23 | 40.44 |
| Delta HBC | 1.68 | 44.04 | 45.24 | 47.61 |
| Hepta Chlor | 3.10 | 5.16 | 3.22 | 2.58 |
| Naphthalene | 2.90 | 6.89 | 0.34 | 30.30 |
| Chlorodane | 0.03 | 66.66 | 66.66 | 66.66 |
| Endosulphane | 3.14 | 7.96 | 1.27 | 29.61 |
| Chlorodane 2 | 0.02 | 100 | 100 | 100 |
| DDE | 1.10 | 16.36 | 18.18 | 20.90 |
| Dieldrine | 1.93 | 17.61 | 18.13 | 19.17 |
| Endosulphane 2 | 2.03 | 30.04 | 30.04 | 49.26 |
| DDD | 3.13 | 17.25 | 7.03 | 25.87 |
| Endrine Aldehyde | 1.03 | 52.42 | 44.66 | 37.86 |
| DDT | 12.61 | 3.41 | 3.72 | 1.90 |
| Endrine Ketone | 1.95 | 44.61 | 36.41 | 30.25 |

TABLE 4

REMOVAL OF SOME ORGANIC COMPOUNDS USING SYNTHESIZED EXTRACTANTS

| Organic compound | the standard conc. (ppm) | % Removal MN octadecyl | % Removal MN-epoxide |
|---|---|---|---|
| Naphthalene | 1.83 | 30.60 | 39.89 |
| Ace naphthalene | 1.89 | 47.61 | 43.38 |
| Ace naphthalene | 2.03 | 42.85 | 41.87 |
| Fluorine | 2.43 | 49.38 | 47.32 |
| Penanthrolene | 2.83 | 59.36 | 56.80 |
| Phenanthrolane | 2.0 | 67.00 | 62.50 |
| Pyrene | 3.10 | 64.19 | 59.03 |
| Flurenthene, also known as Fluoranthene | 3.03 | 66.33 | 58.74 |
| Benz (Anthracene) | 2.96 | 73.64 | 63.51 |
| Triphenylene | 3.29 | 68.38 | 60.18 |
| Benz (Ace Phenthralene), also known as "Benz Ace phenanthroline" | 2.55 | 94.11 | 77.25 |
| Indeno | 10.54 | 50.15 | 46.96 |

Various embodiments and aspects of the invention will now be described in detail with reference to the accompanying figures. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited. Further, whenever a composition, a group of elements or any other expression is preceded by the transitional phrase "comprising", "including" or "containing", it is understood that it is also contemplated the same composition, the group of elements or any other expression with transitional phrases "consisting essentially of", "consisting", or "selected from the group of consisting of", preceding the recitation of the composition, the elements or any other expression.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims, if applicable, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principals of the invention and the practical application, and to enable others of ordinary skill in the art to understand the invention for various embodiments with various modifications as are suited to the particular use contemplated. Accordingly, while the invention has been described in terms of embodiments, those of skill in the art will recognize that the invention can be practiced with modifications and in the spirit and scope of the appended claims.

The foregoing exemplary description and examples have been provided for the purpose of explanation and should not be construed as limiting the invention. While the invention has been described with reference to exemplary embodiments, changes may be made, within the purview of the appended claims, without departing from the scope and spirit of the invention in its aspects. Also, although the invention has been described herein with reference to particular materials and embodiments the invention is not intended to be limited to the particulars disclosed herein; rather, the invention extends to all functionally equivalent structures, methods and uses such as are within the scope of the appended claims.

What is claimed is:

1. A process for removing impurities from an aqueous fluid containing impurities, comprising dispersing magnetic extractants in an aqueous fluid containing impurities, thereby adsorbing the impurities on surfaces of the magnetic extractants and collecting and recovering the adsorbed impurities by magnetic force, wherein the magnetic extractants comprise a plurality of magnetite nanoparticles, and wherein each magnetic nanoparticle includes a plurality of functional groups on a surface thereof, wherein the magnetite nanoparticles have a specific surface area (SSA) of about 47 $m^2/g$ and the functional groups are selected from the group consisting of aldehydes, amines, and epoxides.

2. The process of claim 1, wherein the magnetic extractants are dispersed in the aqueous fluid in a mixer unit, which includes a stirrer.

3. The process of claim 2, wherein the magnetic extractants containing the adsorbed impurities, dispersed in the aqueous fluid, are conducted to a separation unit where the magnetic extractants with the adsorbed impurities adsorbed thereon are collected and recovered.

4. The process of claim 3, wherein the magnetic extractants with the adsorbed impurities are collected and recovered by applying to the magnetic extractants a magnetic field which causes the magnetic extractants to be retained in the separation unit, and substantially clean aqueous fluid, which is substantially free of impurities, is withdrawn from the separation unit.

5. The process of claim 4, wherein the separation unit comprises a mechanism for producing magnetic field, around the separation unit.

6. The process of claim 5, wherein the mechanism for producing the magnetic field is a magnet or an electromagnet.

7. The process of claim 6, wherein the magnetic field is deactivated, after the substantially clean aqueous fluid is withdrawn from the separation unit.

8. The process of claim 7, wherein the magnetic extractants containing the adsorbed impurities are transferred to a collection unit.

9. The process of claim 1, wherein the magnetite extractants have a specific surface area of about 15 to about 26 $m^2/g$.

10. The process of claim 1, wherein the magnetite nanoparticles have a mean particle size of less than about 25 nanometers (nm).

11. The process of claim 10, wherein the magnetite nanoparticles have a mean particle size of about 5 to about 24 nm.

12. The process of claim 10, wherein the magnetite nanoparticles have superparamagnetism properties.

13. The process of claim 1, wherein the magnetite nanoparticles are structured such that they can be repeatedly exposed to magnetic fields without becoming permanently magnetized, which prevents them from magnetically aggregating.

14. The process of claim 13, wherein the magnetite nanoparticles have extensive hydroxyl groups on the surface and couple with silane reagents by the formation of Fe—O—Si covalent bonds.

* * * * *